United States Patent [19]

Nakel et al.

[11] Patent Number: 4,786,510

[45] Date of Patent: Nov. 22, 1988

[54] CALCIUM-IRON MINERAL SUPPLEMENTS

[75] Inventors: Gunther M. Nakel, Aurora, Ind.; David C. Heckert, Oxford, Ohio; Haile Mehansho, Fairfield, Ohio; Sandra L. Miller, Cincinnati, Ohio

[73] Assignee: The Procter & Gamble Company, Cincinnati, Ohio

[21] Appl. No.: 69,352

[22] Filed: Jul. 2, 1987

[51] Int. Cl.$^4$ ............................................ A23L 1/304
[52] U.S. Cl. ..................................... 426/74; 424/147; 424/154; 426/531; 426/549; 426/590; 426/599; 426/648; 426/656; 514/502
[58] Field of Search .................. 426/72, 74, 590, 599, 426/648; 514/502, 905; 424/153, 154

[56] References Cited

U.S. PATENT DOCUMENTS

| 2,325,360 | 7/1943 | Ayers | 99/155 |
|---|---|---|---|
| 3,114,641 | 12/1963 | Sperti et al. | 99/105 |
| 3,657,424 | 4/1972 | Aktins et al. | 424/153 |
| 3,809,773 | 5/1974 | Bookwalter | 426/599 |
| 3,950,547 | 4/1976 | Lamar | 426/656 |
| 3,992,555 | 11/1976 | Kovacs | 426/72 |
| 4,107,346 | 8/1978 | Kravitz | 426/648 |
| 4,214,996 | 7/1980 | Buddemeyer et al. | 252/1 |
| 4,351,735 | 9/1982 | Buddemeyer et al. | 252/1 |
| 4,419,369 | 12/1983 | Nichols | 426/657 |
| 4,486,413 | 12/1984 | Wiesenberger | 426/72 |
| 4,497,800 | 2/1985 | Larson | 426/74 |
| 4,582,709 | 4/1986 | Peters et al. | 426/74 |

FOREIGN PATENT DOCUMENTS

| 75114 | 8/1982 | European Pat. Off. . | |
| 164657 | 12/1985 | European Pat. Off. . | |
| 2219778 | 9/1974 | France . | |
| 54-8767 | 1/1979 | Japan | 426/74 |
| 54-173172 | 8/1981 | Japan . | |
| 2095530 | 10/1982 | United Kingdom . | |

OTHER PUBLICATIONS

Lynch, S. R. and Cook, J. D. (1980), Interaction of Vitamin C and Iron, *Annals New York Academy of Sciences*, 32-44.
Rossander, L., Hallberg, L. and Bjorn-Rasmussen, E. (1979), Absorption of Iron from Breakfast Meals, *Am. J. Clin. Nutr.*, 32, 2484-2489.
Carlson, B. L. and Miller, D. D. (1983), Effects of Product Formulation, Processing and Meal Composition on In Vitro Estimated Availability from Cereal Containing Breakfast Meals, *J. Food Sci.*, 48, 1211-1216.
Kojima, N., Wallace, D. and Bates, W. G. (1981), The Effects of Chemical Agents, Beverages and Spinach on the In Vitro Solubilization of Iron from Cooked Pinto Beans, *Am. J. Clin. Nutr.*, 34: 1392-1401.
Ting, S. V. (1980), Nutrients and Nutrition of Citrus Fruits in "Citrus Nutrition and Quality" (edit. Nagy, S. and Attaway, J.), Amer. Chem. Soc., pp. 3-24.
Gillooly, M., Bothwell, T. M., Torrace, J. D., MacPhail, A. P., Derman, D. P., Bezwoda, W. R., Mills, W., Charlton, R. W. (1983), The Effects of Organic Acids, Phytates and Polyphenols on the Absorption of Iron from Vegetables, *Br. J. Nutr.*, 49, 331-342.
Hallberg, L., Rossander, L. (1984), Improvement in Iron Nutrition in Developing Countries: Comparison of Adding Meat, Soy Protein, Ascorbic Acid, Citric Acid and Ferrous Sulfate on Iron Absorption for a Simple Latin American Type of Meal, *Am. J. Clin. Nutr.*, 39: 577-583.
Kelly, S. E., Chawla-Singh, K., Sellin, J. M., Yasillo, N. J., Rosenberg, I. M. (1984), Effects of Meal Composition on Calcium Absorption: Enhancing Effect of Carbohydrate Polymer, *Gastroenterol*, 87, 596-600.
*Remington's Pharmaceutical Sciences*, 15th Ed., 393 (1975).
*The Pharmacological Basis of Therapeutics*, 5th Ed., 1315-1316 (1975).
Kletzien, S. W., Iron Metabolism, *J. Nutr.*, 19, 187-197.
Chapman, D. G., Campbell, J. A. (1957), Effect of Calcium and Phosphorus Salts on the Utilization of Iron by Anaemic Rats, *Br. J. Nutr.*, 11, 127-133.
Dunn, J. A. (1968), The Effects of Dietary Calcium Salts and Fat on Iron Absorption in the Rat, *S. Afr. J. Med. Sci.*, 33, 65-70.
Barton, J. C., Conrad, M. E., Parmley, R. J. (1983), Calcium Inhibition of Inorganic Iron Absorption in Rats, *Gastroenterology*, 84, 90-101.
Dawson-Hughes, B., Seligson, F. H., Hughes, V. A. (1986), Effects of Calcium Carbonate and Hydroxyapatite on Zinc and Iron Retention in Postmenopausal Women, *Am. J. Clin. Nutr.*, 44, 83-88.
Seligman, P. A., Caskey, J. H., Frazier, J. L., Yucker, R. M., Podell, E. R., Allen, R. M. (1983), Measurements of Iron Absorption from Prenatal Multivitamin-Mineral Supplements, *Obstetrics and Gyn.*, 61, 356-362.
Metrevely, E. G., "Latent Iron Deficiency and Effect of Prophylactic Administration of Medicamentous Iron on the RedBlood Composition of Healthy Young Children", *Pediatriyc* (Moscow), 1977, vol. 12, pp. 17-19.

Primary Examiner—Donald E. Czaja
Assistant Examiner—Carolyn Paden
Attorney, Agent, or Firm—Jerry J. Yetter; Leonard W. Lewis

[57] ABSTRACT

Nutritional mineral supplements comprise a mixture of a calcium source, especially calcium citrate-malate, and an iron-sugar complex, especially iron sucrate-malate. Food and beverage compositions, especially juice beverages, supplemented with these calcium and iron materials are disclosed.

15 Claims, No Drawings

CALCIUM-IRON MINERAL SUPPLEMENTS

TECHNICAL FIELD

The present invention relates to mineral supplements which contain certain calcium and iron compounds, and foods and beverages containing same.

BACKGROUND OF THE INVENTION

Vitamin and mineral supplements for human and veterinary use are commonplace. Recently, it has become recognized that certain groups of the human population may require quite high intakes of minerals, such as calcium, to prevent or alleviate certain disease states, for example, osteoporotic conditions. The medical management of certain anemias can be handled rather well by increasing the daily intake of iron. Some diets, or heavy physical exercise, may require the intake of considerable quantities of minerals apart from those generally obtained through what otherwise would be considered a balanced diet.

Mineral supplements, such as those commercially available, are useful in many circumstances where enhanced mineral uptake is desirable. However, adhering to a regimen which requires the separate intake of mineral supplements can give sub-optimal results, simply because the regimen requires a change in the normal habits and practices of the user. It would be more convenient if the minerals could be included in ordinary foods and beverages, so that they would be ingested without extra attention, planning and implementation on the part of the user.

There are well-recognized problems associated with adding mineral supplements to foods and beverages. For example, many calcium supplements tend to be rather insoluble, and, therefore, not very useful in beverages, or tend to have a "chalky" taste or mouth feel. Iron supplements tend to discolor foodstuffs, or to be organoleptically unsuitable. Moreover, it is particularly difficult to formulate foods and, especially, beverages, containing mixtures of calcium supplements and iron supplements, inasmuch as these minerals tend to interact. This interaction not only affects the organoleptic and aesthetic properties of the foods and beverages, but also undesirably affects the nutritional bioavailability of these minerals, themselves.

It would be desirable, therefore, to have mixed calcium and iron supplements which are compatible and nutritionally available. It would also be quite useful to have such supplements which could be added to food and beverage compositions without undesirably affecting organoleptic or aesthetic properties.

It is an object of the present invention to provide calcium-iron mineral supplements which fulfill these unmet needs.

It is a further object of this invention to provide foodstuffs, beverages and beverage concentrates which are supplemented with calcium and iron.

These and other objects are secured herein, as will be seen from the following disclosure.

BACKGROUND ART

Certain forms of calcium citrate-malate are disclosed for use as mineral supplements, including beverages; see Japanese Application No. Sho 54-173172, date of application 28 Dec. 1979, laid-open No. Sho 56-97248, 5 Aug., 1981; and see also French Pat. No. 2,219,778 (Application No. 73.08643).

Some form of iron sucrate has been administered to children and the effect on Hb reported; see the Russian reference Metreveli, E. G., PEDIATRIYA (Moscow) 1977, (12), 17–19; C. Abs. 89: 637.

*Remington's Pharmaceutical Sciences*, 15th Ed., 393 (1975) indicates that ferrous and ferric ions form soluble coordination complexes with many agents such as ammonium salts, citrates, tartrates, amines, sugar and glycerine, which protect the iron from precipitation by the usual iron precipitants. Iron gluconate and fumarate salts are said to be employed as hematinics.

Goodman and Gilman, *The Pharmacological Basis of Therapeutics*, 5th Ed., 1315–1316 (1975) reports that iron salts have many incompatibilities and should be prescribed alone, preferably between meals, for maximal absorption, but just after meals if necessary to minimize gastric symptoms. Gastrointenstinal absorption of iron is reportedly adequate and essentially equal from the following six ferrous salts: sulfate, fuamarate, gluconate, succinate, glutamate, and lactate. Absorption of iron is lower from ferrous citrate, tartrate, pyrophosphate, etc. Reducing agents such as ascorbic acid and some chelating agents such as succinic acid may increase absorption of iron from ferrous sulfates, but are said to be not worth the extra cost because of the high efficacy of ferrous sulfate when administered alone. Ferrous sulfate is reported to have a saline, astringent taste, and is mixed with glucose or lactose to protect it against oxidation, when used as an iron supplement.

European Pat. No. 164,657 to Pfeiffer and Langden relates to an iron dextran, which is obtained by adding precipitated ferric hydroxide to dextran produced by adding sucrose solution to a solution of D-glucose and dextran-sucrose enzyme.

U.S. Pat. No. 4,582,709, to Peters and Derick, Apr. 15, 1986, relates to chewable mineral supplements, and lists, inter alia, various calcium and iron compounds.

U.S. Pat. No. 4,351,735, to Buddemeyer, et al, Sept. 28, 1982, relates to mineral supplements which contain certain phosphate moieties. Dispersibility of the compositions is said to be enhanced by "hydroxyl sources", e.g., sugars.

U.S. Pat. No. 4,214,996, to Buddemeyer, et al, July 29, 1980, relates generally to the same subject matter as the U.S. Pat. No. 4,351,735, above, but claims, inter alia, iron compositions and calcium compositions.

The beneficial effect of orange juice on the uptake of iron from dietary sources is described by Carlson and Miller in JOURNAL OF FOOD SCIENCE 48, 1211 (1983).

U.S. Pat. No. 2,325,360, to Ayres et al, issued July 27, 1943, discloses a method for replacing gases removed during deaeration of fruit juices, such as orange juice, with carbon dioxide. In this method, dry calcium carbonate, or a mixture of calcium carbonate and citric acid, is dropped into a can which is then filled with deaerated orange juice. (Other organic acids such as malic and tartaric acid can be used in place of citric acid.)

U.S. Pat. No. 3,657,424, to Akins et al, issued Apr. 18, 1972, discloses the fortification of citrus juices, including orange juice, with sodium, calcium and chloride ions in amounts beyond what is naturally present in the juice. Calcium salts which can be used in fortification include the chlorides, citrates or phosphates, although calcium chloride is preferred for providing the desired chloride ion.

U.S. Pat. No. 3,114,641, to Sperti et al, issued Dec. 17, 1963, discloses extended orange juice products obtained by diluting single-strength orange juice or concentrated orange juice. To maintain the flavor of the diluted orange juice product, materials such as calcium chloride, magnesium chloride, sodium or potassium citrates, tartaric and malic acids (or their salts) are included.

British patent specification No. 2,095,530, published Oct. 6, 1982, discloses a process for obtaining an acid beverage enriched in protein, particularly a fruit juice or fruit-flavored beverage. In this process, an aqueous suspension of soy protein is prepared using water and/or fruit juice. Calcium in a concentration of from 5 to 50 mM is added, after which the pH of the suspension is reduced and the insoluble material separated to yield a protein solution. A fruit juice or fruit flavoring can then be added to this protein solution. The calcium can be added in the form of the chloride, acetate, tartrate, malate or lactate salt.

European patent application No. 75,114, published Mar. 30, 1983, discloses protein-containing fruit juice drinks enriched with vitamins and minerals. These drinks contain 30–90% fruit juice (a mixture of 20–70% apple juice, 4–40% white grape juice, 1–10% passionfruit juice and 5–25% lemon juice), 2 to 20% whey protein concentrate, and a mineral salt mixture of potassium, sodium, magnesium, calcium and phosphate. Calcium is present in these drinks at 0.01 to 0.3%, preferably at 0.02 to 0.03%.

SUMMARY OF THE INVENTION

The present invention encompasses nutritional mineral supplements which comprise a mixture of a nutritionally supplemental amount of a calcium source, especially calcium citrate-malate, and a nutritionally supplemental amount of an iron-sugar complex. The counterions associated with the iron-sugar complexes herein are preferably members selected from the group consisting of malate (most preferred), citrate, tartrate, ascorbate, and mixtures thereof. Preferred supplements contain iron sucrate-malate, iron fructate-malate, or mixtures thereof. Preferably, the iron in the complexes comprises ferrous iron, but ferric iron is also acceptable.

The invention also encompasses food, beverage or beverage concentrate compositions which comprise:
 (a) a foodstuff, beverage or beverage concentrate;
 (b) a nutritionally supplemental amount of a calcium supplement, most preferably calcium citrate-malate; and
 (c) a nutritionally supplemental amount of an iron-sugar complex, preferably a member selected from the group consisting of iron sucrate-malate (most preferred), iron fructate-malate, iron sucrate-citrate, iron fructate-citrate, iron sucrate-ascorbate, iron fructate-ascorbate, or mixtures thereof. Again, the iron is preferably in the ferrous state.

Typical of the compositions of this invention are beverage or beverage concentrates which comprise:
 (a) at least about about 0.1% by weight of fruit or cola flavor, or at least about 3% by weight of fruit juice;
 (b) a nutritionally supplemental amount of calcium citrate-malate; and
 (c) a nutritionally supplemental amount of an iron-sugar complex, most preferably iron II sucrate-malate.

By way of example, the fruit juice in such compositions can be selected from grape juice, pear juice, passionfruit juice, pineapple juice, banana juice or banana puree, apricot juice, orange juice, lemon juice, grapefruit juice, apple juice, cranberry juice, tomato juice, tangarine juice, and mixtures thereof.

The invention encompasses beverages, especially juice and cola beverages, which are carbonated in the manner of soft drinks, as well as "still" beverages. The invention also encompasses nectars and full-strength beverages or beverage concentrates which contain at least abvout 45% by weight of juice.

The nutritional supplements herein are particularly useful with beverages or beverage concentrates made from orange juice or grapefruit juice.

As will be disclosed more fully hereinafter, the mineral supplements of this invention can conveniently be used in powder, tablet, chewable lozenge, capsule or liquid form, for enteral or parenteral nutrition, and in combination with conventional foodstuffs, such as breads, cakes, snacks, infant formulations, meat analogs and extenders, spreads, and the like.

All ratios, proportions and percentages herein are by weight, unless otherwise specified.

DETAILED DESCRIPTION OF THE INVENTION

The present invention involves the conjoint use of nutritionally-supplemental amounts of calcium and iron compounds in humans and lower animals.

By "nutritional" or "nutritionally-supplemental amount" herein is meant that the mineral sources used in the practice of this invention provide a nourishing amount of said minerals. In mineral supplements such as tablets or powders, this supplemental amount will comprise at least 3% of the Recommended Daily Allowance (RDA) of the daily intake of said mineral, as defined in The United States of America (see Recommended Daily Dietary Allowance—Food and Nutrition Board, National Academy of Sciences—National Research Council). More generally, mineral supplements will contain at least 10%, more typically 50% to 300%, of the RDA per unit dose of the supplement. In food or beverage products of the type disclosed herein, the nutritionally supplemental amount will generally comprise more than 3% of the RDA, preferably 10%–100% RDA, most preferably 10%–30% of the RDA, per unit portion of the food or beverage product. Of course, it is recognized that the preferred daily intake of any mineral may vary with the user. For example, pregnant, lactating, or post-menopausal females may require an increased intake of calcium, over the usual RDA. Persons suffering with anemia may require an increased intake of iron. Such matters are familiar to physicians and nutritional experts, and usage of the compositions of the present invention may be adjusted accordingly.

In general, the RDA (calcium) will range from 360 mg per 6 Kg for infants to 1200 mg/54–58 Kg female, depending somewhat on age. The RDA (iron) ranges from 10 mg per 6 Kg to 18 mg per 54–58 Kg female, depending somewhat on age. As is well-known, it is possible to overdose with iron supplements, especially in males, with deleterious effects to the liver. Typically, foods and beverages are supplemented with only about 10–15% RDA iron (based per serving) to account for iron which is available from other dietary sources (assuming a reasonably balanced diet), thereby avoiding this problem. Moreover, it can be difficult to supplement beverages with more than 20-30% RDA of calcium (based per serving) without encountering precipitation and/or organoleptic problems. However, this level of supplementation is equivalent to cow's milk in calcium value, and is quite acceptable. Of course, if iron toxicity and organoleptic quality are not deemed important considerations in individual circumstances, more of the supplements herein can be used.

The preparation of the preferred calcium source used herein, "calcium citrate-malate", is described hereinafter in considerable detail.

The "iron-sugar" complexes used in the practice of this invention are prepared in the manner described more fully hereinafter. (These materials are referred to herein as "complexes", but they may, in fact, exist in solution as complicated, highly-hydrated, protected colloids. However, the term "complex" is used herein for simplicity.) While the iron in these complexes can be in the ferric (iron III) state, it is more preferably in the ferrous (iron II) state. Ferrous iron is better tolerated and utilized by the body than ferric iron. Importantly, feric iron and common ferrous salts can cause off-flavors in some beverages, after storage; ferric iron can also oxidize and thus degrade ascorbic acid (Vitamin C) in citrus beverages. The preferred complexes used herein can conveniently be thought of as iron-sugar-carboxylate complexes, wherein the carboxylate provides the counterion for the ferrous (preferred) or ferric iron. While not intending to be limited by theory, it is believed that the acceptable taste of these iron complexes is due to the relatively large sizes of the sugar moiety and carboxylate counterion, which mask the usual "well-water" and/or brackish flavor of some iron supplements.

The overall synthesis of the preferred iron-sugar-carboxylate complexes used in the practice of this invention involves:

(a) forming a calcium-sugar moiety in aqueous media, for example, by reacting calcium hydroxide with a sugar;

(b) reacting an iron source, such as ferrous ammonium sulfate, with the calcium-sugar moiety in aqueous media to provide an iron-sugar moiety; and (c) neutralizing the reaction system with a carboxylic acid, for example, malic acid, to provide the desired iron-sugar complex.

The preferred iron II-sucrate-malate complex prepared in this manner is essentially equivalent to ferrous sulfate in iron bioavailability (measured as % change in hematocrit of test animals over the range of 0-9 ppm Fe), and, most importantly, is organoleptically acceptable in beverages, especially citrus beverages.

The "sugars" which can be employed in the practice of this invention include any of the ingestible saccharidic materials, and mixtures thereof, well-known in the culinary arts. For example, glucose, sucrose and fructose can conveniently be employed, with sucrose and fructose being the more preferred. However, other saccharidic materials can be used, for example mannose, galactose, lactose, maltose, and the like.

The "carboxylate counterion" used in the preparation of the preferred iron-sugar complexes herein can be any ingestible carboxylate species. However, some judgment must be made with regard to flavor contribution. For example, citrate, malate and ascorbate yield ingestible complexes whose flavors are judged to be quite acceptable, particularly in fruit juice beverages. Tartaric acid is acceptable, particularly in grape juice beverages, as is lactic acid. Longer-chain fatty acids may be used in solid mineral supplements, but can affect flavor and water solubility. For essentially all purposes, the malate (preferred), citrate and ascorbate moieties suffice, although others can be selected, according to the desires of the formulator.

In a less preferred mode, the counterion for the iron-sugar complex can be noncarboxylate moieties such as phosphate, chloride, sulfate, or the like. However, such counterions can undesirably interact with calcium ions, especially in beverages. In high concentrations, these counterions may contribute an undesirable flavor note, Accordingly, the carboxylate counterions noted above are preferred herein.

The present invention is particularly suited for the preparation of juice beverages and beverage concentrates, particularly orange juice. The concentrated orange juice, orange juice aroma and flavor volatiles, pulp and peel oils used in the method of the present invention can be obtained from standard orange juice processing. See Nagy et al, *Citrus Science and Technology*, Volume 2, (AVI Publishing Co. 1977), pp 177-252 (herein incorporated by reference) for standard processing of oranges, grapefruit and tangerines. (See also Nelson et al, *Fruit and Vegetable Juice Processing Technology* (3rd Ed., AVI Publishing 1980), pp. 180-505 (herein incorporated by reference) for standard processing of noncitrus juices such as apple juice, grape juice, pineapple juice, etc. to provide sources of juice and juice materials for mineral-supplemented noncitrus juice products). Fresh juice is extracted from the oranges, principally of the Valencia type. (The peel of the oranges is initially rasped to provide peel oils which can be used in the method of the present invention.) Juices from different oranges are frequently blended to adjust the sugar to acid ratio. A sugar to acid ratio of from about 8:1 to about 20:1 is considered acceptable. However, preferred sugar to acid ratios are typically from about 11:1 to about 15:1.

Juice is extracted from the oranges by using automatic juicing machines, or less often by hand squeezing of the oranges. The type of equipment used to extract the juice is not critical. The raw juice exiting from the squeezing device contains pulp, rag and seeds. The rag and seed are separated from the juice and pulp in a finisher. The juice is then typically separated into a pulp portion and a serum portion. (The pulp portion can be used as a source of pulp in the method of the present invention.)

The serum portion can be concentrated by a variety of techniques which typically include evaporative concentration or freeze concentration. In evaporative concentration, the serum portion of the juice is passed through an evaporator (e.g., falling film or temperature accelerated short time evaporator [TASTE] type). Water vapor, as well as the aroma and flavor volatiles, are stripped from the juice. These stripped volatiles are then centrifuged to provide an upper layer (essence oils) and a lower layer (aqueous essence). (A portion of these essence oils and aqueous essence are typically used as the source of orange juice aroma and flavor volatiles for the method of the present invention.) The remaining stripped juice is then concentrated in the evaporator (by heat) to the appropriate amount of solids as measured by the sugar content of the concentrated juice. This concentrated juice can then be used in the method of present invention.

Most concentrated orange juices are obtained by evaporative concentration. However, freeze concentration can also be used to obtain concentrated orange juice useful in the method of the present invention. Freeze concentration typically involves passing the serum portion of the juice through a scraped wall heat exchanger to form substantially pure ice crystals which are then separated from the concentrated juice. A preferred freeze concentration method is disclosed in U.S. Pat. No. 4,374,865 to Strobel, issued Feb. 22, 1983, which is incorporated by reference. Unlike evaporative concentration, concentrated orange juice obtained by freeze concentration typically contains the aroma and flavor volatiles as well.

Method for Preparing Beverages and Beverage Concentrates Supplemented with Calcium and Iron The preferred overall method for preparing the liquid compositions herein involves preparing premix solutions of the calcium and iron complexes (see Examples I, II and III, hereinafter) and admixing the premixes to the liquid compositions. The following discussion of this method will generally be with regard to formation of orange juice beverages and juice concentrates, which are highly preferred fruit juice products according to the present invention. However, this method can also be used to prepare iron- and calcium-supplemented beverages and concentrates, especially those based on other citrus juices such as grapefruit juice, noncitrus juices such as apple juice, as well as mixtures of juices.

In general, an acid component comprising citric acid and malic acid is typically dissolved in the appropriate quantity of water. (If desired, fruit juice or concentrated fruit juice such as lemon juice can be used to supply a portion of the acids.) Generally, this acid component comprises from 0 to about 90% by weight citric acid and from about 10 to 100% by weight malic acid. For orange juice, this acid component typically comprises from about 20 to about 90% by weight citric acid and from about 10 to about 80% by weight malic acid. Preferably, this acid component comprises from about 5 to about 60% by weight citric acid and from about 40 to about 95% by weight malic acid. (For noncitrus juices such as apple juice, this acid component typically comprises from about 5 to about 80% by weight citric acid and from about 20 to about 95% by weight malic acid, and preferably comprises from about 20 to about 50% by weight citric acid and from about 50 to about 80% by weight malic acid.) As a rule, the ratio of these acids is selected to provide optimum flavor character in the juice.

Once the solution containing the dissolved acids is formed, a source of calcium is then added. Calcium carbonate ($CaCO_3$) is a preferred calcium source. This calcium source leads to the greatest and most rapid initial solubilization of calcium and causes the least amount of off-flavor generation. Calcium hydroxide [$Ca(OH)_2$] and calcium oxide (CaO) are also acceptable calcium sources, but can cause more off-flavor generation than calcium carbonate. The weight ratio of total acids to calcium added in the solution is typically from about 0.5 to about 12. Preferably, this weight ratio is from about 1 to about 6.

Addition of calcium carbonate, calcium oxide, or calcium hydroxide to the aqueous solution of acids provides a premix containing soluble and solubilizable calcium. This is due to the fact that highly soluble calcium citrate and malate species such as CaHcitrate, Ca($H_2$citrate)$_2$, and CaHmalate are formed in the solution due to the reaction between the calcium source and the acids. Without added stabilizers, the highly soluble calcium citrate species are stable in the premix solution for periods up to only about a few hours. After this short period of time, the highly soluble citrate species tend to disproportionate to the corresponding acid and the more thermodynamically stable, insoluble calcium citrate salts, such as $Ca_3$citrate$_2$.

To improve the stability of the more soluble calcium malate and especially citrate species in the premix solution, it is preferred in the method of the present invention to include a premix stabilizer. Materials which can complex with calcium and/or act as crystallization inhibitors are useful as premix stabilizers. These materials include sugars, such as sucrose, glucose, fructose, high fructose corn syrup, invert sugar, and polysaccharides such as pectin, algins, hydrolyzed starches, xanthan gum, and other edible gums. Concentrated juices which naturally contain both sugars and polysaccharides are particularly suitable premix stabilizers. Preferred premix stabilizers are sucrose and high fructose corn syrup (especially for extended juice products) and concentrated orange juice having a sugar content of from about 35° to about 80° Brix whose source is described hereafter.

The premix stabilizer can be added immediately after the calcium source is added to the aqueous solution containing the acids. (When calcium carbonate is the calcium source, carbon dioxide evolution is preferably allowed to substantially cease before the premix stabilizer is added.) However, if desired, the premix stabilizer (especially in the case of sugars and concentrated juice) can be added to the aqueous solution of the acids prior to addition of the calcium source. The amount of premix stabilizer included in the premix solution typically depends upon the stabilizer used. When sugars are used as the premix stabilizer, they are typically added in an amount sufficient to provide a sugar content of from about 2° to about 40° Brix. When polysaccharides are used, the amount can vary widely, but is typically from about 0.01 to about 0.5% on a weight/volume basis. When concentrated juice is used as the premix stabilizer, it is typically included in an amount sufficient to provide a sugar content of from about 2° to about 40° Brix (preferably from about 2° to about 24° Brix).

The premix solution of solubilized and solubilizable calcium is typically prepared in a batch-type fashion, as in the description above, at room temperature. However, this premix solution can also be prepared in a continuous fashion. In this continuous method, the ingredients (water, acids, calcium source and optional premix stabilizer) are constantly metered together to form the premix solution. The level at which the ingredients are metered is adjusted, as necessary, to insure appropriate solubilization of the calcium in the premix solution and to provide the appropriate acidity.

Separately, a premix solution of the iron-sugar complex is prepared. In general, this solution is somewhat simpler to prepare than the calcium citrate-malate solution, above, since precipitation is not a major problem. Thus, a calcium-sugar reaction product is treated with an iron (preferably iron II) source, and the reaction product is neutralized with a carboxylic acid, in the manner of Example III, below.

The premix solution containing the solubilized calcium and the premix containing the solubilized iron are combined in a mix tank with chilled (e.g., below about 4.4° C.) concentrated orange juice having a sugar content of from about 35° to about 80° Brix (preferably from about 60° to about 70° Brix), orange juice aroma and flavor volatiles, plus other orange juice materials such as pulp and peel oils, to provide iron- and calcium-supplemented orange juice products. The particular proportions of premix solution, concentrated juice, aroma and flavor volatiles, pulp and peel oils used will depend upon a number of different factors, including the type of orange juice product involved (single-strength juice beverage or juice concentrate). For example, iron- and calcium-supplemented 42° Brix orange juice concentrates can be prepared by combining 65 parts concentrated orange juice (65° Brix), 5 parts pulp, 15 parts of an aroma/flavor concentrate, 0.4 parts peel oil with the 15 parts Fe/Ca premix. Similar single-strength juice beverages can be prepared by appropriate variation of the amounts of concentrated orange juice, pulp, aroma/flavor concentrate, peel oil and premix solutions, as well as the inclusion of water.

Juice compositions and other beverages are preferably formulated at a pH below about 4.3, generally about 3.7-4.0, for reasons of microbial stability.

After the iron- and calcium-supplemented orange juice product is obtained, it is then filled into cans, cartons, bottles or other appropriate packaging. In the case of orange juice concentrates, these products are typically frozen after being filled into cans.

The following examples illustrate the practice of this invention but are not intended to be limiting thereof.

EXAMPLE I

Preparation of Calcium Citrate-Malate

A calcium citrate-malate solution is prepared by dissolving 2 parts sucrose and then 0.1 part citric and 0.28 part malic acids in 28.19 parts water. Calcium hydroxide (0.22 part) is added and the mixture is agitated. This solution can be used directly to prepare beverages, or can be freeze-dried to use in solid mineral supplements.

EXAMPLE II

Preparation of Calcium Citrate-Malate Without Sugar

In an alternate mode, the sucrose can be deleted from the above preparation. Thus, a calcium citrate-malate solution is prepared by admixing 62 g calcium carbonate with 11 g citric acid and 44 g malic acid in 1,040 g water. This solution can be used to prepare low calorie beverages, beverage concentrates, or freeze-dried for use in solid supplements.

EXAMPLE III

Preparation of Iron II Sucrate-Malate

Sucrose (85.5 g) is dissolved in water (299.8 g), making sure that dissolution is complete. Calcium hydroxide (18.5 g) is then added, and the mixture is stirred for 5 minutes. Any clouding is observed, and the resulting solution is filtered through a glass filter paper.

To the resulting calcium-sucrate solution is added ferrous ammonium sulfate hexa-hydrate (24.5 g), and the solution is covered air-tight (e.g., SARAN wrap). The green color indicates the iron is in the desired II oxidation state.

To the above solution is added malic acid (33.5 g) in 3 batches, to pH 3-4. The precipitated calcium malate is filtered through standard filter paper, but the filter cake comprising calcium sulfate is not rinsed. The resulting solution comprises the iron sucrate-malate used in the practice of this invention. The solution can be used per se, or can be freeze-dried to provide the iron sucrate-malate in powder form.

EXAMPLE IV

Mixed Composition

The calcium citrate-malate composition of Example II and the iron sucrate-malate composition of Example III are, separately, freeze-dried and ground to a fine powder. The powders are mixed to provide individual unit doses comprising 1,200 mg calcium and 20 mg iron. The mixed powders are packaged in soluble gelatin capsules for oral ingestion as a calcium-iron mineral supplement.

EXAMPLE V

Mixed Composition

In an alternate mode, a calcium and iron supplement powder mixture is prepared from the calcium citrate-malate of Example I and the iron sucrate-malate of Example III, and adjusted in bulk with powered lactose to provide a mineral supplement powder which delivers 1,500 mg calcium and 10 mg iron per 10 g dose.

EXAMPLE VI

Beverage Compositions

The following beverage compositions (a-g) are fortified with the calcium and iron compositions of Examples I and III to provide 20% RDA of calcium and 10% RDA of iron per 180 ml serving:
  (a) "sparkling" orange juice comprising 55% orange juice and 45% carbonated water;
  (b) pear-grapefruit nectar comprising 25% pear juice, 20% grapefruit juice, the balance comprising 10% sucrose-water;
  (c) kiwi-grapefruit drink comprising 20% kiwi fruit juice, 15% grapefruit juice, the balance comprising water;
  (d) mixed fruit "cocktail" comprising 10% each of the juices of passion fruit, mango, guava, pineapple, papaya, banana, apricot, mandarin orange, pear and lime juices;
  (e) yogurt/fruit beverage comprising 20% milk products, 1% pectin, 20% pineapple juice, 10% shredded pineapple fruit pulp, 16% corn syrup, the balance comprising water;
  (f) cola beverage comprising 0.35% cola flavor emulsion, 11% sugar, 0.1% phosphoric acid, 0.1% citric and malic acids, caramel coloring, the balance comprising carbonated water;
  (g) full-strength apple juice (using the calcium citrate-malate of Example II in place of the Example I material).

EXAMPLE VII

Food Compositions

The following food compositions (a-f) are fortified with the mixed calcium-iron composition of Example IV to provide 100% RDA of calcium and 20% RDA of iron per 250 g serving;
  (a) salted potato snack product comprising moistened, comminuted potato flakes, shaped and deep-fried in the form of saddle-shaped chips;
  (b) peanut butter product comprising finely ground peanuts, up to 3% peanut oil, salt;

(c) cookie product comprising inner core of flour, shortening, flavoring and fructose enrobed in outer layer of flour, shortening, flavoring and sucrose;
(d) brownie snack product comprising commercial DUNCAN HINES brownie mix;
(e) soy-based meat analog product comprising a 50:1 (wt.) mixture of de-oiled soybean meal and egg whites, extruded, in patty or chunk form;
(f) infant formulation in powder or liquid form comprising sterilized soy powder or soy "milk", vanilla flavor, preservative.

It should be appreciated that the calcium source in the solid food compositions and the solid unit dosage forms herein need not be restricted to calcium citrate-malate for organoleptic/stability reasons, as in the case of beverages and beverage concentrates. Materials such as calcium chloride, hydroxide, carbonate, etc., can alternatively be used. However, the superior bioavailability of calcium from calcium citrate-malate makes this the preferred calcium supplement for use in the practice of this invention with solid foods and supplements, as well as with beverages and beverage concentrates.

EXAMPLE VIII

Mineral Supplement

A powdered mineral supplement comprises 2,000 mg calcium carbonate and 15 mg iron (II) fructate-malate, prepared in the manner of Example XX, hereinafter.

EXAMPLE IX

Orange Juice Concentrate

A highly preferred orange juice concentrate comprises:

| Ingredient | Amount (g) |
|---|---|
| 65° Brix orange juice concentrate | 2070 |
| Aqueous orange essences | 550 |
| Orange pulp | 270 |
| Orange oil | 2 |
| Orange flavor mix | 14 |
| Calcium citrate-malate premix solution of Example I | To 800 mg $Ca^{++}$/ 180 ml portion* |
| Ferrous sucrate-malate premix solution of Example III | To 7.2 mg $Fe^{++}$/ 180 ml portion* |

*When diluted to single strength

EXAMPLE X

Orange Juice or Nectar

The concentrate of Example IX can be diluted with water to provide a single-strength orange juice.

In an alternate mode, the concentrate of Example IX is diluted to 45% juice levels with sugar-water to provide an orange nectar.

EXAMPLE XI

Iron- and calcium-fortified chewable lozenges comprise:

| Ingredient | Amount |
|---|---|
| Iron II sucrate-ascorbate | 20 mg |
| Calcium citrate-malate | 500 mg |
| Dextrose | 5 g |
| Fruit flavor* | 6 mg |

| Ingredient | Amount |
|---|---|
| Color | As desired |

*Fruit flavors used herein generally comprise synthetically reconstituted flavor esters. In this example, pineapple flavor is used, and comprises a synthetic mixture of ethyl acetate, acetaldehyde, methyl n-valerate, methyl i-valerate, methyl i-caproate and methyl caprylate.

The lozenge of Example XI is prepared by mixing the ingredients and compacting the mixture in a standard press.

*Fruit flavors used herein generally comprises synthetically reconstituted flavor esters. In this example, pineapple flavor is used, and comprises a synthetic mixture of ethyl acetate, acetaldehyde, methyl n-valerate, methyl i-valerate, methyl i-caproate and methyl capyrlate.

The following examples illustrate syntheses of various iron compositions which can be used in the practice of this invention.

EXAMPLE XII

Iron II Sucrate-Malate

Sucrose (1368 g; 4 moles) is dissolved in water (3995 g), making sure all sugar is dissolved. Calcium hydroxide (148 g; 2 moles) is added to the sugar-water and stirred for 5 minutes. The solution is filtered through a glass filter.

To the calcium-sucrate solution is added iron II ammonium sulfate (196 g; 0.5 moles) and covered air-tight with SARAN WRAP. The color should remain green. Malic acid (268 g; 2 moles) is added in three batches. At each addition, a pH reading is taken with litmus paper to insure pH 3-4. The precipitate is filtered-off with a paper filter, and the filter cake is not rinsed. The compound is in the filter liquor.

EXAMPLE XIII

Iron II Sucrate-Malate

Sucrose (684 g; 2 moles) is dissolved in water (2226 g), making sure all sugar is dissolved. Calcium hydroxide (74 g; 1 mole) is added to the sugar-water and stirred for 5 minutes. The solution is filtered through a glass filter.

To the calcium-sucrate solution is added iron II ammonium sulfate (196 g; 0.5 mole) and the solution is covered air-tight with SARAN WRAP. The color should remain green. Malic acid (268 g; 2 moles) is added in three batches. At each addition, a pH reading is taken with litmus paper to insure pH 3-4. The precipitate is filtered (paper filtered), and the filter cake is not rinsed. The title compound is in the filter liquor.

EXAMPLE XIV

Iron II Sucrate-Malate

Sucrose (684 g; 2 moles) is dissolved in water (2856 g), making sure all sugar is dissolved. Calcium hydroxide (148 g; 2 moles) is added and the solution is stirred for 5 minutes. The solution is filtered through a glass filter.

To the calcium sucrate solution is then added iron II ammonium sulfate (392 g; 1 mole) and the system is covered air-tight with SARAN WRAP. The green color should remain. Malic acid (268 g; 2 moles), is added in three batches. At each addition, a pH reading is taken with litmus paper to insure pH 3-4. The precipitate is filtered (paper filter) and the filter cake is not rinsed. The title compound is in the filter liquor.

EXAMPLE XV

Iron II Fructate-Malate

Fructose (360 g; 2 moles) is dissolved in water (1644 g), making sure all fructose is dissolved. Calcium hydroxide (148 g; 2 moles) is added to the fructose solution and stirred for 5 minutes. The solution is filtered through a glass filter.

To the calcium fructose solution is added iron II ammonium sulfate (196 g; 0.5 mole) and the solution is covered air-tight with SARAN WRAP. The color should remain green. Malic acid (268 g; 2 moles) is added in three batches. At each addition, a pH reading is taken with litmus paper to insure pH 3-4. The precipitate is filtered off (paper filter). The title compound is in the filter liquor.

EXAMPLE XVI

Iron II Sucrate-Citrate

Sucrose (684 g; 2 moles) is dissolved in water (2399 g), making sure all sugar is dissolved. Calcium hydroxide (148 g; 2 moles) is added to the solution and stirred for five minutes. The solution is filtered through a glass filter. To the calcium-sucrate solution is added iron II ammonium sulfate (196 g; 0.5 mole) and the solution is covered air-tight with SARAN WRAP. The green color should persist. Citric acid (384 g; 2 moles) is added to the reaction mixture in three batches. At each point of addition, a pH reading is taken with litmus paper to insure pH 3-4. The precipitate is filtered-off (paper filter) and the filter cake is not rinsed. The title compound is in the filter liquor.

EXAMPLE XVII

Iron II Sucrate-Tartrate

Sucrose (684 g; 2 moles) is dissolved in water (2399 g), making sure all sugar is dissolved. Calcium hydroxide (148 g; 2 moles) is added to the sugar solution and stirred for 5 minutes. The solution is filtered through a glass filter.

To the calcium-sucrate solution is added iron II ammonium sulfate (196 g; 0.5 mole) and the solution is covered air-tight with SARAN WRAP. The green color should persist. Tartaric acid (300 g; 2 moles) is added to the solution in three batches. At each time of addition, a pH reading is taken with litmus paper to insure pH 3-4. The precipiate is filtered (paper filter) and removed; the filter cake is not rinsed. The title compound is in the filter liquor.

EXAMPLE XVIII

Iron II Glucate/Fructate-Malate

Glucose (360 g; 2 moles) and fructose (360 g; 2 moles) are co-dissolved in water (1643 g), making sure all sugar is dissolved. Calcium hydroxide (148 g, 2 moles) is added to the sugar-water and stirred for 5 minutes. The solution is filtered through a glass filter.

To the calcium/mixed sugars solution is added iron II ammonium sulfate (196 g; 0.5 moles) and the solution is covered air-tight with SARAN WRAP. The green color should persist. Malic acid (268 g; 2 moles) is added in three batches. At each addition, a pH reading is taken with litmus to insure pH 3-4. The precipitate is filtered-off (paper filter) and the filter cake is not rinsed. The title compound is in the filter liquor.

EXAMPLE XIX

Iron II Sucrate-Citrate/Ascorbate

Sucrose (684 g; 2 moles) is dissolved in water (2399 g), making sure all sugar is dissolved. Calcium hydroxide (148 g; 2 moles) is added to the sugar water solution and stirred for 5 minutes. The solution is filtered through a glass filter.

To the calcium-sucrate solution is added iron II ammonium sulfate (196 g; 0.5 mole) and the solution is covered air-tight with SARAN WRAP. The green color should persist. The citric acid (192 g; 1 mole) is first added to the solution, then the ascorbic acid (352 g; 2 moles) is added in three batches. At each time of addition, a pH reading is taken with litmus paper to insure pH 3-4. The precipitate is filtered (paper filter). The title compound is in the filter liquor.

EXAMPLE XX

Iron II Fructate Malate

Fructose (541 g; 3 moles) is dissolved in water (1672 g), making sure all is dissolved. Calcium hydroxide (37 g; 0.5 moles) is added and stirred for 5 minutes. The solution is filtered through a glass filter.

To the calcium-fructose solution is added iron II sulfate (139 g; 0.5 mole), and the solution is covered air-tight with SARAN WRAP. The color should remain green. Malic acid (67 g; 0.5 moles) is added to the solution in three batches. At each addition, a pH reading is taken with litmus paper to insure pH 3-4. The precipitate is filtered-off (paper filter) and the filter cake is not rinsed. The title compound is in the filter liquor.

Potentiators

The foregoing compositions function exceptionally well as mixed iron-calcium supplements. However, it has now also been determined that certain materials act as "potentiators", which still further enhance the bioavailability of calcium. Fructose is one such potentiator, and other carbohydrates, such as sucrose, function similarly, albeit less well than fructose.

However, iron bioavailability is somewhat impaired by the administration of calcium, and this impairment remains, even in the presence of usually-found levels of carbohydrates, including fructose.

It has not been found that citric acid (or citrates) and tartaric acid (tartrates) partially alleviate calcium's inhibitory effect on iron, and mixtures of citric/ascorbic acid (or citrate/ascorbate mixtures), do overcome the inhibitory effect.

Accordingly, in a preferred mode, this invention also uses a potentiating amount of citrate; or, preferably, citrate/ascorbate; or, citrate/fructose; or, citrate/ascorbate/fructose, or like tartrate combinations, to potentiate iron and calcium bioavailability when these minerals are administered conjointly. It will be appreciated by the formulator that these potentiators can simply be added to the above-exemplified compositions, if not already inherently present.

By "potentiating amount" of the citrate, tartrate, ascorbate, carbohydrate (especially fructose), and mixtures thereof, materials used herein is meant an amount sufficient to enhance uptake and bioavailability of iron and calcium when administered to humans or lower animals. Of course, even small amounts of these potentiators have some beneficial effect. However, it is preferred to use sufficient potentiator to provide bioavailability levels of the iron/calcium mixtures which are essentially equivalent to iron and calcium supplements when administered separately, and several hours apart. Fortunately, the potentiators used herein are entirely safe for consumption, so there is essentially no upper limit to the amount that can be safely ingested. Moreover, in practical terms, the potentiators are inexpensive, so there is no need for the formulator to carefully balance benefit/cost ratios. Typically, then, the citrate, tartrate and ascorbate potentiators are used in a weight ratio with the minerals (calculated as iron and calcium per se, discounting associated ions or ligands) of potentiator:mineral ranging from 1000:1 to 1:3, generally 3:1 to 1:1. The fructose potentiator may be used in much higher ratios, say, $10^6$:1, since the formulator may also find it useful to include fructose, not only for its potentiating effect, but also for its bulk sweetener effect.

EXAMPLE XXI

Mineral Supplement

A powdered mineral supplement comprises 2,000 mg calcium citrate-malate, 15 mg iron (II) fructate-malate prepared in the manner of Example XX, 250 mg citric acid and 100 mg ascorbic acid.

What is claimed is:

1. A nutritional mineral supplement, comprising a mixture of:
   (i) a nutritionally supplemental amount of a calcium source; and
   (ii) a nutritionally supplemental amount of an iron-sugar complex.

2. A mineral supplement according to claim 1 wherein the calcium source is calcium citrate-malate.

3. A mineral supplement according to claim 2 wherein the counterion of the iron-sugar complex is selected from malate, citrate, tartrate, ascorbate, or mixtures thereof.

4. A mineral supplement according to claim 3 wherein the iron-sugar complex is iron sucrate-malate, iron fructate-malate, or mixtures thereof.

5. A supplement according to claim 3 wherein the iron is in the ferrous state.

6. A food, beverage or beverage concentrate composition, comprising:
   (a) a foodstuff, beverage or beverage concentrate;
   (b) a nutritionally supplemental amount of a calcium supplement; and
   (c) a nutritionally supplemental amount of an iron-sugar complex.

7. A composition according to claim 6 wherein the calcium supplement is calcium citrate-malate.

8. A composition according to claim 6 wherein the iron-sugar complex is iron sucrate-malate, iron fructate-malate, iron sucrate-citrate, iron fructate-citrate, iron sucrate-ascorbate, iron fructate-ascorbate, or mixtures thereof.

9. A composition according to claim 8 wherein the iron is in the ferrous state.

10. A beverage or beverage concentrate composition according to claim 6, which comprises:
    (a) at least about 0.1% by weight of fruit or cola flavor, or at least 3% by weight of fruit juice;
    (b) a nutritionally supplemental amount of calcium citrate-malate; and
    (c) a nutritionally supplemental amount of an iron-sugar complex.

11. A composition according to claim 10 wherein the fruit juice is selected from grape juice, pear juice, passionfruit juice, pineapple juice, banana juice or banana puree, apricot juice, orange juice, lemon juice, grapefruit juice, apple juice, cranberry juice, tomato juice, and mixtures thereof.

12. A composition according to claim 11 wherein the iron-sugar complex is iron II sucrate-malate.

13. A juice beverage according to claim 12 which is carbonated.

14. A beverage or beverage concentrate according to claim 12 which contains at least about 60% by weight of juice.

15. A beverage or beverage concentrate according to claim 14 which comprises orange juice or grapefruit juice.

* * * * *

UNITED STATES PATENT AND TRADEMARK OFFICE
CERTIFICATE OF CORRECTION

PATENT NO. : 4,786,510
DATED : November 22, 1988
INVENTOR(S) : G. M. Nakel, D. C. Heckert, H. Mehansho, S. L. Miller It is certified that error appears in the above-identified patent and that said Letters Patent is hereby corrected as shown below:

Column 14, line 39, "not" should be --now--

Signed and Sealed this

Thirtieth Day of July, 1991

*Attest:*

HARRY F. MANBECK, JR.

*Attesting Officer*  *Commissioner of Patents and Trademarks*